(12) United States Patent
Lasseur et al.

(10) Patent No.: US 8,445,531 B2
(45) Date of Patent: May 21, 2013

(54) RODENTICIDAL COMPOUNDS, COMPOSITION INCLUDING SAME AND USE THEREOF FOR CONTROLLING HARMFUL RODENTS

(75) Inventors: Romain Lasseur, Bully (FR); Etienne Benoit, Lyons (FR); Philippe Berny, Vaugneray (FR); Stephane Besse, Francheville (FR)

(73) Assignee: Liphatech, Pont du Casse (FR)

( * ) Notice: Subject to any disclaimer, the term of this patent is extended or adjusted under 35 U.S.C. 154(b) by 0 days.

(21) Appl. No.: 13/579,945

(22) PCT Filed: Feb. 16, 2011

(86) PCT No.: PCT/FR2011/050326
§ 371 (c)(1),
(2), (4) Date: Aug. 20, 2012

(87) PCT Pub. No.: WO2011/101591
PCT Pub. Date: Aug. 25, 2011

(65) Prior Publication Data
US 2012/0316231 A1    Dec. 13, 2012

(30) Foreign Application Priority Data
Feb. 18, 2010  (FR) ..................................... 10 51155

(51) Int. Cl.
*A01N 43/16* (2006.01)
*C07D 311/56* (2006.01)

(52) U.S. Cl.
USPC ............................ 514/457; 549/285; 549/286

(58) Field of Classification Search
USPC .................................. 549/285, 286; 514/457
See application file for complete search history.

(56) References Cited

U.S. PATENT DOCUMENTS 2,872,457 A   2/1959  Schroeder et al.
2,952,689 A   9/1960  Enders et al.

FOREIGN PATENT DOCUMENTS
WO      99/01446      1/1999

OTHER PUBLICATIONS

International Search Report dated Jul. 8, 2011, corresponding to PCT/FR2011/050326.
Gebauer et al.; "Synthesis and Structure-Activity Relationships of Novel Warfarin Derivatives"; vol. 15, No. 6; Feb. 15, 2007.

*Primary Examiner* — Kristin Bianchi
(74) *Attorney, Agent, or Firm* — Young & Thompson

(57) ABSTRACT

A rodenticidal compound of formula (I): as well as the isomers thereof, in particular enantiomers, diastereoisomers, tautomers or mixtures of isomers in all proportions, where: R1 is: H or (II) or (III) with X=H, OH, Cl, Br, F or N0$_2$; R2 is: (IV) or (V) or (VI) with X=H, OH, Cl, Br, F or NO$_2$; R3 is: O or S or (VII) with X=H, OH, Cl, Br, F or N0$_2$. Compositions containing such compounds as well as a method of use thereof in controlling harmful rodents are also described.

12 Claims, No Drawings

RODENTICIDAL COMPOUNDS, COMPOSITION INCLUDING SAME AND USE THEREOF FOR CONTROLLING HARMFUL RODENTS

This invention relates to the field of rodenticidal products, i.e., products that have the property of killing certain rodents.

The object of the invention is in particular new molecules that have a rodenticidal effect as well as the compositions that integrate them. It also relates to the use of these molecules and compositions for combating rodent pests.

The damage caused by certain pests such as rats or mice has been known for a long time, and the risks linked to their presence are serious.

In addition to the material damage that they can cause in particular to electrical systems, rodent pests primarily constitute a significant medical risk. Directly, or by their parasites, they are at the origin of numerous diseases transmitted to humans and to domestic animals, such as tetanus, streptobacillosis, pasteurellosis, leptospirosis, salmonellosis, hemorrhagic fever, or else plague.

This is why, for a number of years, different de-infestation systems have been developed: physical systems, for example based on mechanical traps, adhesives or else ultrasound, and chemical systems, in particular repellant products, chemosterilizers or rodenticides.

Even if the use of physical systems is developing, the control of rodent populations is always done for the most part by means of attack methods using rodenticides, in particular for reasons of effectiveness in the event of massive infestations.

The rodenticides belong to very diverse chemical families: anticoagulants, convulsants, cardiotoxic agents, cytotoxic agents, or hypercalcemic agents. Most of the rodenticides that are used today are anticoagulants, in particular anticoagulants that are derived from hydroxy-4-coumarin or coumaphene such as coumachlor, coumatetralyl, difenacoum or brodifacoum, difethialone or bromadiolone and anticoagulants that are derived from indanedione-1,3 such as chlorophacinone, and diphacinone.

The metabolism of the anticoagulants is characterized by good oral absorption and an essentially hepatic distribution. These products are therefore very effective. They act by accumulation over several days until the death of the animal is produced by acute anemia, without suffering and without arousing the suspicion of its fellow creatures toward the product.

However, the rodenticidal anticoagulants that currently exist have a high remanence and persist for a long time in the carcasses of rodents that have ingested them. However, since these are non-selective toxic products, the species that prey on rodents, in particular birds of prey and small wild or domestic mammals, can themselves be poisoned by these anticoagulants that are stored in the carcasses.

There is therefore a need for a product that makes it possible to combat rodents effectively while protecting untargeted wildlife from secondary poisoning.

T0 respond to this, this invention proposes a new compound that has a rodenticidal action that is at least as effective as the existing anticoagulants, but whose storage period in the liver is not adequate for producing secondary poisoning.

In particular, the object of the invention is a compound that corresponds to the formula (I):

(I)

as well as its isomers, in particular enantiomers, diastereoisomers, tautomers or mixtures of isomers in any proportions, in which:

R1 represents: H or

R2 represents:

R3 represents: O or S or with X=H, OH, Cl, Br, F or $NO_2$,
with X able to be different or identical in R1, R2 or R3.

The object of the invention is also a process for the production of a compound of formula (I) starting from 4-hydroxy-coumarin.

Another object of the invention relates to rodenticidal compositions that comprise at least one compound that corresponds to the formula (I). Preferably, these compositions come in the form of powders, blocks, gels, pastes, impregnated grains, or else in liquid form.

Finally, the object of the invention is also the use of a compound of formula (I) or a composition that includes it for controlling the rodent population.

Advantageously, the molecules according to the invention combine a true rodenticidal effectiveness on all of the rodents with a very low hepatic remanence. Their use therefore makes possible effective combating of rodents while considerably reducing the risk of secondary poisoning.

Other characteristics and advantages will emerge from the following detailed description of the invention.

According to a first aspect, the invention therefore relates to a compound that corresponds to the formula (I) below:

(I)

in which:
R1 represents: H or with X=H, OH, Cl, Br, F or $NO_2$

R2 represents:

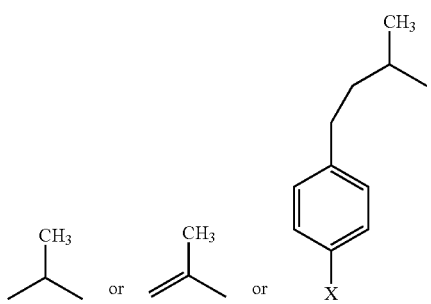

with X=H, OH, Cl, Br, F or NO$_2$

R3 represents: O or S or

with X=H, OH, Cl, Br, F or NO$_2$.

The object of the invention is also the isomers of this compound of formula (I), in particular enantiomers, diastereoisomers, tautomers, or mixtures of isomers in any proportions.

The compounds that correspond to this formula (I) and its isomers have a rodenticidal activity.

Preferably, R3 represents an oxygen O.

According to a preferred and particularly suitable variant, the object of the invention is a specific compound that corresponds to the formula (I) in which:
R1 represents H,
R3 represents O, and
R2 represents:

This specific compound has the following formula (II):

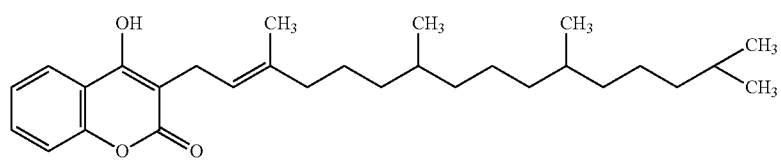 [SMILES: C/C(=C\Cc1c(O)c2ccccc2oc1=O)CCCC(C)CCCC(C)CCCC(C)C]

According to another variant, the compound according to the invention corresponds to the formula (I) in which:
R1 represents

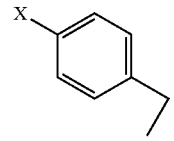

R2 represents

R3 represents O.

This specific compound has the following formula (III):

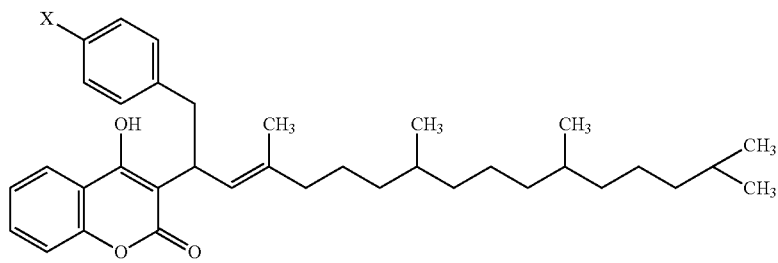

The compound according to the invention can also correspond to the formula (I) in which:
R1 represents

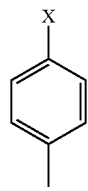

R2 represents

and
R3 represents O.

This specific compound has the following formula (IV):

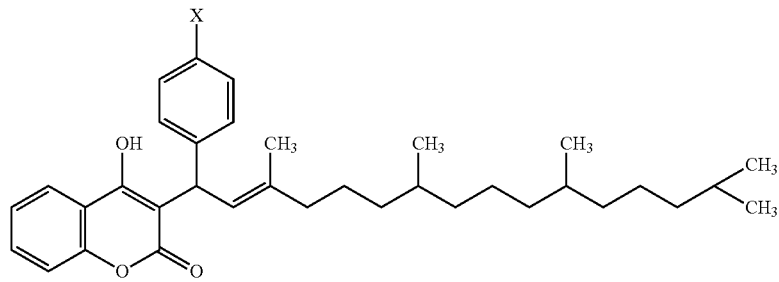

According to another embodiment, the compound according to the invention can also correspond to the formula (I) in which:
R1 represents H,
R3 represents O, and
R2 represents

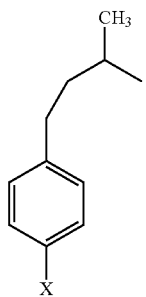

This particular compound has the following formula (V):

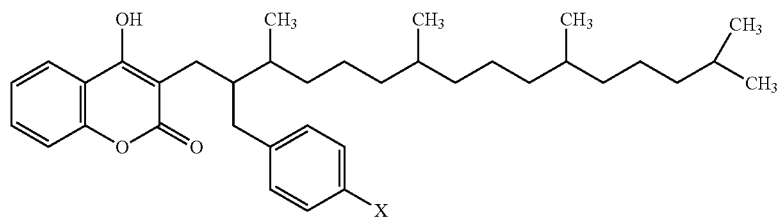

The compounds according to the invention can be obtained by grafting a branched lateral aliphatic chain, which is potentially more or less substituted, on a 4-hydroxycoumarin.

The process for obtaining a compound of formula (I) according to the invention can therefore be shown in diagram form as follows:

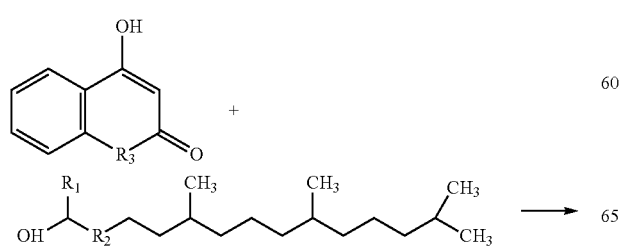

-continued

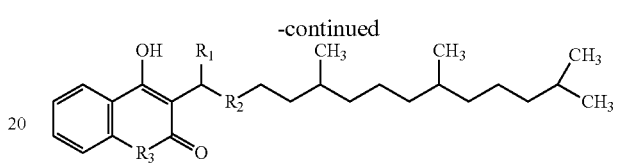

with:
R1 representing: H or

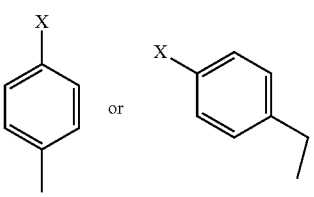

R2 representing:

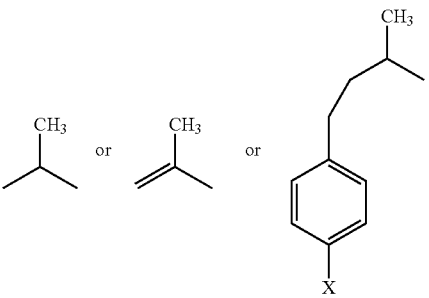

R3 representing: O or S or

with X representing H, OH, Cl, Br, F or $NO_2$, X being able to be different or identical in R1, R2 or R3.

The grafting of the aliphatic chain can be done by any suitable grafting process. It can be carried out in particular by a Michael addition reaction using a bromine-containing derivative.

By way of example, the particular compound of formula (II) can be obtained by the implementation of the following stages:
- Synthesis of phytyl bromide from phytol and carbon bromide, and
- Synthesis of 3-phytyl-4-hydroxy-coumarin from 4-hydroxy-coumarin and phytyl bromide in an ethanolic alkaline medium.

The synthesis of phytyl bromide from phytol and carbon bromide is a reaction of halogenation on a primary alcohol, which takes place at ambient temperature in the presence of triphenyl phosphine and carbon tetrabromide in a dichloromethane medium for two hours. The synthesized phytyl bromide is purified by successive washing cycles with solutions of $NaHCO_3$, $H_2O$ and brine. The crude product that is obtained is concentrated and used as is.

The synthesis of 3-phytyl-4-hydroxy-coumarin from 4-hydroxy-coumarin and phytyl bromide is a C-alkylation reaction that corresponds to the attack by alkyl halide on a charged carbon of the coumarinic cycle in position 3. The reaction takes place in an alkaline medium so as to make possible in a first step the formation of a phenolate ion that contributes to greatly shifting the electronic charge that is carried by the carbon in position 3. In a second step, the phytyl bromide reacts in an ethanolic medium. The reaction medium is next purified by a series of selective liquid-liquid extractions. Then, two isomers (cis and trans) of the compound of formula (II) are obtained.

The compounds of formula (I) according to the invention, in particular the specific compounds of formula (II), (III), (IV) or (V), as well as their isomers, have a significant rodenticidal effect, even at low concentration.

They can be incorporated in compositions that are designed to combat rodent pests.

The invention therefore also has as its object rodenticidal compositions that include at least one compound of formula (I) as active material.

Preferably, the object of the invention is rodenticidal compositions that comprise between 0.001 and 50% by weight of a compound that corresponds to the formula (I), even more preferably between 0.001 and 20%.

The compositions according to the invention can come in any form that is suitable for combating rodent pests. They can come in particular in the form of liquid concentrate, powder, grains, gels, pastes, or bait extruded as pellets or as blocks.

In addition to the compound of formula (I), the compositions according to the invention contain several vehicles: one or more vehicles that comprise the matrix that contains the rodenticidal compound, and one or more vehicles whose role is technological or biological.

The vehicles that are used in the matrix can be selected in particular from among mineral oils, carbohydrates such as dextrins, mineral materials such as clay, glycols, and other organic solvents such as DMSO, water, grain raw materials such as barley, wheat, corn or rice, and binders such as paraffin.

The other vehicles that are often used are, for example, additives to which rodents are partial or additives to attract rodents such as sugar or aromas, preservatives, or else bitter agents that are designed to reduce the risk of accidental consumption by children or domestic animals.

The compositions according to the invention can be manufactured by a thorough and homogeneous mixing of the active compound(s) of formula (I) with ingredients of the substrate. This simplicity of embodiment is possible in particular because of the small amount of active compound required to obtain the desired rodenticidal effect.

The mixture of the active material and vehicles can be done according to any suitable processes, in particular by convection, diffusion and/or shearing. The mixture can be produced, for example, in the double-jacketed tanks that make possible a cooling or a heating of the mixture, if necessary.

One example of a suitable composition according to the invention that is designed to come in the form of extruded bait comprises the following compounds:
- Grain raw materials (wheat, barley, corn, rice), preferably between 40 and 70% by weight of the composition,
- A paraffin- or water-type binder, preferably between 15 and 40% by weight of the composition,
- A compound of formula (I), preferably between 0.001 and 50% by weight of the composition,
- A bitter agent of the denatonium benzoate type,
- One or more preservatives of the family of organic acids and their salts such as ascorbic acid, propionic acid, or potassium sorbate, and
- A dye, preferably the green dye PG7.

The manufacturing of the continuously extruded substrate comprises the following stages:
- Mixing ingredients using a convection mixer,
- Extrusion using a single-screw extruder or a two-screw extruder, with a diameter of 30 mm to 100 mm, between 55° C. and 95° C.,
- Shaping,
- Cutting up bait with a mass of between 5 and 100 g,
- Stabilization by heat treatment: cooling by pulsed air for 30 minutes or by convection drying for 2 to 10 hours, and
- Packaging.

The compounds of formula (I) and the compositions according to the invention can be used to combat rodent pests.

The rodenticidal compositions that comprise the compounds of formula (I) can be applied for prevention or treatment in zones to be protected from rodent attacks. They can optionally be inserted or attached in bait boxes suitable for fighting rodents so as to secure their use.

Advantageously, the compounds of formula (I) according to the invention have a very good rodenticidal effectiveness, at least as significant as the existing anticoagulant rodenticides, while having a very low hepatic remanence. Actually, the compounds according to the invention are stored in the liver for a very limited time.

Their use therefore makes possible an effective fight against rodents while protecting untargeted wildlife from secondary poisoning.

They can be used in particular in the domestic setting, in a rural, professional, or urban setting, in restoration sites or sites of public gatherings, or else in the farm produce industry for combating rats, mice, field mice, common rats and/or any other rodent pest.

The dose of the compound that is to be administered depends on the targeted rodent. It is preferably between 0.5 mg and 100 mg based on the rodent in question.

The invention is now illustrated by an example and test results that show the claimed effects.

EXAMPLE OF A PROCESS FOR OBTAINING A SPECIFIC COMPOUND OF FORMULA (I), THE COMPOUND OF FORMULA (II)

The process consists of the implementation of two stages: synthesis of phytyl bromide from phytol and carbon tetrabromide, and synthesis of the compound of formula (II), the 3-phytyl-4-hydroxy-coumarin, from 4-hydroxy-coumarin and phytyl bromide in an ethanolic alkaline medium.

a. Synthesis of Phytyl Bromide

Phytyl bromide can be obtained by the implementation of the following stages:
- Into a lapped-column flask, introduce: phytol (10 mmol) and dichloromethane that contains triphenyl phosphine; an excess of 20 to 30% is necessary for entirely consuming the phytol,
- Stir with a magnet,
- Add carbon tetrabromide all at once; the solution that is obtained is clear and slightly light yellow,
- Allow to react for 2 hours at ambient temperature.

Next, the purification of the reaction medium is carried out by liquid-liquid extractions:
- Add 50 ml of an $NaHCO_3$-saturated solution,
- Stir and eliminate the aqueous phase,
- Wash the organic phase with distilled water,
- Stir and eliminate the aqueous phases,
- Dry-evaporate the organic phase under a stream of nitrogen,
- Take up the dry residue with hexane or cyclohexane,
- Filter the hexane phase on a Whatman filter,
- Wash the precipitate with hexane or cyclohexane, and then
- Dry-evaporate the hexane or cyclohexane.

An orangey oily residue is obtained.

b. Synthesis of 3-Phytyl-4-OH-Coumarin

The 3-phytyl-4-hydroxy-coumarin can be obtained by implementing the following stages:
- Introduce the following into a flask: 4-hydroxy-coumarin (10 mmol), 4 mmol of a 1 M NaOH solution (4 mmol), and 10 mmol of a 10 M NaOH solution for total solubilization, in such a way as to obtain a slightly light yellow solution,
- Stir with a magnet at 70° C. for 30 minutes, to make possible the formation of coumarin phenolate,
- Add phytyl bromide (7.3 mmol), and then ethanol,
- Stir with a magnet at 70° C. for 2 hours; the reaction medium gradually turns dark red.

The purification of the reaction medium is carried out by liquid-liquid extractions (during these operations, all of the liquid phases are chromatographed by HPLC):
- Add 1 M soda into the medium until obtaining a medium at pH 14,
- Wash with toluene, allow it to decant, and recover the oily interface with the alkaline phase,
- Extract the toluene phases with a 1 M NaOH solution and eliminate them,
- Reassemble the alkaline phases that are red in color and extract them using ethyl acetate,
- Eliminate the alkaline aqueous phase and wash the ethyl acetate phase with an HCl solution,
- Eliminate the acidic aqueous phases and wash the ethyl acetate phase with distilled water,
- Eliminate the aqueous phases and filter ethyl acetate on anhydrous sodium sulfate,
- Wash sodium sulfate with ethyl acetate, and
- Evaporate ethyl acetate by sub-sack under a stream of nitrogen.

The final product comes in the form of an orangey-yellow oil. The molecules that are obtained correspond to the formula (II).

Evaluation of the Effectiveness and the Remanence on Rats of the Product of Formula (II)

The rodenticidal effectiveness and the remanence of the compounds according to the invention have been tested in comparison with the rodenticidal product of reference bromadiolone, with bromadiolone being the least remanent of all of the second-generation anticoagulants currently used in combating rodents.

For this test, the compound of formula (II) that is obtained by implementing the process disclosed above is used.

The operating procedure is disclosed below.

3 lots of 5 rats were used for the compound of formula (II), and 2 lots of 4 rats were used for bromadiolone.

For the Compound of Formula (II):

3 doses of 10 mg/kg of rat were administered intraperitoneally in succession at T0, T24h and T48h.

1 lot of rats was used to follow the mortality rate brought about by the 3 administrations of the compound of formula (II) according to the invention.

1 lot of rats was used to follow the coagulation time between 24 hours and 120 hours after the first injection. Actually, the coagulation time is the first parameter that varies and tends toward infinity under the action of an anticoagulant.

1 lot of rats was used to carry out a metering of residue of the compound of formula (II) in the liver at T72h, T96h and T120h.

For Bromadiolone:

Doses of 2 mg/kg/day were administered for 4 days.

1 lot of rats was used to determine the mortality rate brought about at T120h.

A metering of bromadiolone residue in the liver at T120h was carried out.

1 lot of rats was used to follow the coagulation time between 24 hours and 120 hours after the first injection.

Results

The results that are obtained are presented below:

| | | T0 | T24 h | T48 h | T72 h | T96 h | T120 h | Total Mortality |
|---|---|---|---|---|---|---|---|---|
| Compound According to the Invention | Mortality Follow-Up | / | 2 Deaths | 2 Deaths | 1 Death | / | / | 100% |
| | Coagulation Time Follow-Up (Seconds) | Infinite | Infinite | Infinite | Infinite | Infinite | 120 | / |

| | | T0 | T24 h | T48 h | T72 h | T96 h | T120 h | Total Mortality |
|---|---|---|---|---|---|---|---|---|
| | Liver Residue Follow-Up (μg/g) | / | / | / | 0.65 | 0.51 | 0.37 | / |
| Bromadiolone | Mortality Follow-Up | / | / | / | / | 2 Deaths | 2 Deaths | 100% |
| | Coagulation Time Follow-Up (s) | Infinite | Infinite | Infinite | Infinite | Infinite | Infinite | / |
| | Liver Residue Follow-Up (μg/g) | / | / | / | / | / | 4.2 | / |

These results first show that the injection of compounds according to the invention makes it possible to bring about the death of 100% of the treated rats, just like the reference rodenticidal product.

Furthermore, 120 hours after the first injection, the coagulation time remains infinite for bromadiolone whereas it decreases to 120 seconds for the compound according to the invention. This reflects a rapid metabolization of the compound of formula (II), a phenomenon that is not observed for bromadiolone.

In addition, a rapid decrease in the metering of residue of the compounds according to the invention is noted between 72 hours and 120 hours after the first injection, and a low remanence is noted in the rat livers. In comparison, the results that are obtained with bromadiolone 120 hours after the first injection show the presence of 11 times more residue, whereas 30 mg of the compound of formula (II) has been administered versus only 8 mg of bromadiolone.

These results therefore demonstrate a rapid metabolism of the compounds according to the invention in rodents, in parallel with a high effectiveness on this target.

The invention claimed is:

1. A compound that corresponds to the formula (I):

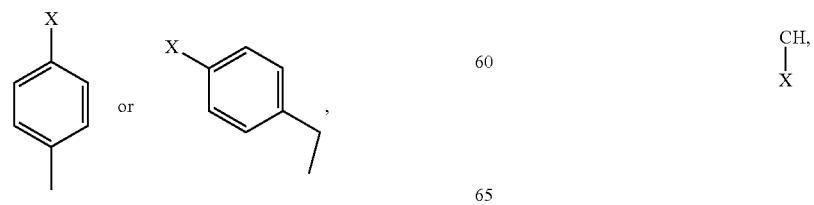

and isomers thereof selected from the group consisting of enantiomers, diastereoisomers, tautomers, and mixtures thereof in any proportions, wherein:

R1 represents: H or

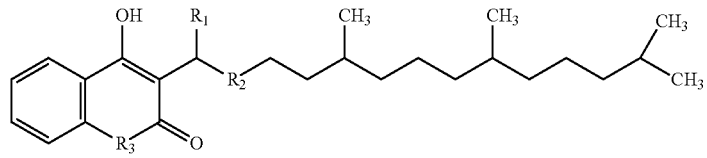

with X=H, OH, Cl, Br, F or NO$_2$,

R2 represents:

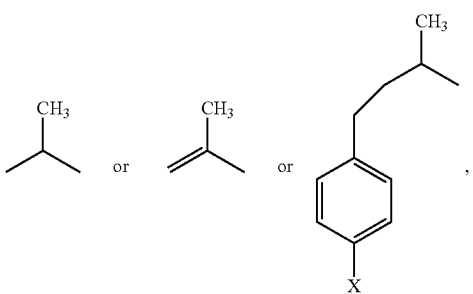

with X=H, OH, Cl, Br, F or NO$_2$,

R3 represents: O or S or $$\overset{CH_{,}}{\underset{X}{|}}$$

with X=H, OH, Cl, Br, F or NO$_2$.-

2. The compound according to claim 1, wherein the compound corresponds to the following formula (II):

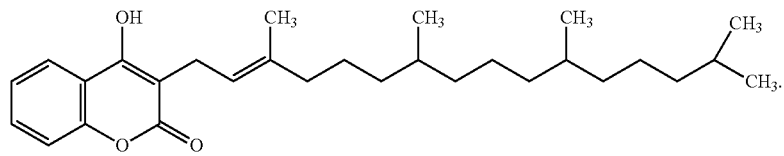 [SMILES: C/C(=C\Cc1c(O)c2ccccc2oc1=O)CCCC(C)CCCC(C)CCCC(C)C]

3. The compound according to claim 1, wherein the compound corresponds to the following formula (III):

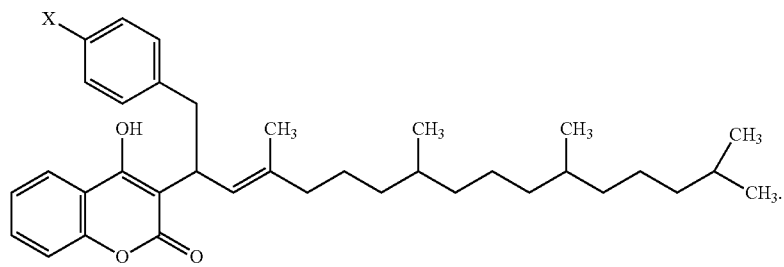

4. The compound according to claim 1, wherein the compound corresponds to the following formula (IV):

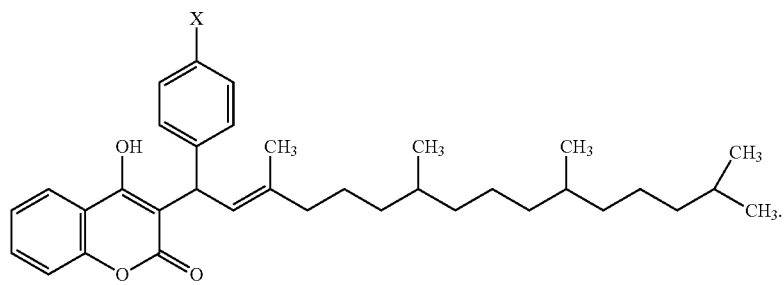

5. The compound according to claim 1, wherein the compound corresponds to the following formula (V):

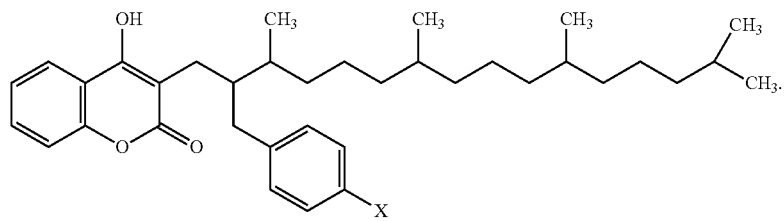

6. A rodenticidal composition, comprising at least one compound according to claim 1.

7. A rodenticidal composition according to claim 6, wherein the rodenticidal composition comprises between 0.001 and 50% by weight of said compound.

8. A rodenticidal composition according to claim 6, wherein the rodenticidal composition is in a form selected from the group consisting of liquid concentrate, powder, grains, gels, pastes, and bait that is extruded as pellets or as blocks.

9. A process for combating rodent pests comprising applying an effective amount of a rodenticidal composition according to claim 6 to a zone so as to treat or protect said zone from rodent attacks.

10. The process according to claim 9, wherein the zone is in a location selected from the group consisting of a domestic setting, a rural setting, a professional setting, and urban setting and the process is for combating rats, mice, field mice, common rats and/or any other rodent pest in said location.

11. The process according to claim 9, wherein the zone is in a restoration site or a site of public gatherings, and the process is for combating rats, mice, field mice, common rats and/or any other rodent pest in said sites.

12. The process according to claim 9, wherein the zone is in the farm produce industry, and the process is for combating rats, mice, field mice, common rats and/or any other rodent pest in the farm produce industry.

* * * * *